US009354517B2

(12) United States Patent
Kon et al.

(10) Patent No.: US 9,354,517 B2
(45) Date of Patent: May 31, 2016

(54) RESIST COMPOSITION AND METHOD FOR FORMING PATTERN

(71) Applicant: FUJITSU LIMITED, Kawasaki-shi, Kanagawa (JP)

(72) Inventors: Junichi Kon, Isehara (JP); Yoshihiro Nakata, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/078,882

(22) Filed: Nov. 13, 2013

(65) Prior Publication Data

US 2014/0272706 A1 Sep. 18, 2014

(30) Foreign Application Priority Data

Mar. 18, 2013 (JP) .................................. 2013-055228

(51) Int. Cl.
| G03F 7/004 | (2006.01) |
|---|---|
| G03F 7/075 | (2006.01) |
| G03F 7/038 | (2006.01) |
| G03F 7/20 | (2006.01) |
| C07F 7/08 | (2006.01) |

(52) U.S. Cl.
CPC ............ *G03F 7/0757* (2013.01); *C07F 7/0852* (2013.01); *G03F 7/0043* (2013.01); *G03F 7/0382* (2013.01); *G03F 7/20* (2013.01)

(58) Field of Classification Search
CPC ........ G03F 7/0382; G03F 7/20; C07F 7/0852
USPC .......... 430/270.1, 311, 322, 325, 329; 528/43
See application file for complete search history.

(56) References Cited

U.S. PATENT DOCUMENTS

| 5,252,686 A | * | 10/1993 | Aoai et al. ..................... 525/480 |
|---|---|---|---|
| 6,632,585 B1 | * | 10/2003 | Nakamura ................. 430/281.1 |
| 8,828,642 B2 | * | 9/2014 | Kamogawa et al. ........ 430/270.1 |
| 2010/0052062 A1 | | 3/2010 | Fukui |
| 2010/0215839 A1 | * | 8/2010 | Rantala et al. ............... 427/96.1 |
| 2011/0008730 A1 | * | 1/2011 | Hanamura et al. .......... 430/270.1 |
| 2012/0122036 A1 | * | 5/2012 | Sugita et al. .................. 430/325 |
| 2012/0237873 A1 | * | 9/2012 | Fujiwara et al. ............ 430/280.1 |
| 2012/0302688 A1 | * | 11/2012 | Karkkainen ................... 524/320 |
| 2013/0216952 A1 | * | 8/2013 | Yokoyama et al. ........ 430/286.1 |
| 2014/0113230 A1 | * | 4/2014 | Kim et al. .................. 430/270.1 |
| 2014/0134544 A1 | * | 5/2014 | Anno et al. ................... 430/325 |
| 2014/0178822 A1 | * | 6/2014 | Wu et al. .................... 430/285.1 |
| 2014/0335452 A1 | * | 11/2014 | Yokoyama et al. ........ 430/270.1 |

FOREIGN PATENT DOCUMENTS

| JP | 2001081404 A | * | 3/2001 |
|---|---|---|---|
| JP | 2006-278506 A1 | | 10/2006 |
| JP | 2010-56156 A1 | | 3/2010 |
| JP | 2012-53243 A1 | | 3/2012 |
| TW | 201111916 | | 4/2011 |

OTHER PUBLICATIONS

Taiwanese Office Action dated Dec. 22, 2014 in counterpart Taiwanese Patent Application No. 102141449 (with English summary based on cited art).

* cited by examiner

*Primary Examiner* — Amanda C Walke
(74) *Attorney, Agent, or Firm* — Kratz, Quintos & Hanson, LLP (57) ABSTRACT

A resist composition includes: a solvent; and a resin in the solvent, the resin being prepared by the hydrolysis and condensation of an alkoxy group-containing compound that contains an alkoxy group bound to a silicon atom or a germanium atom in the presence of an acid or an alkali, wherein a portion of the resist composition irradiated with an energy radiation is insoluble in a developing solution.

10 Claims, 4 Drawing Sheets

RESIST COMPOSITION AND METHOD FOR FORMING PATTERN

CROSS-REFERENCE TO RELATED APPLICATION

This application is based upon and claims the benefit of priority of the prior Japanese Patent Application No. 2013-055228 filed on Mar. 18, 2013, the entire contents of which are incorporated herein by reference.

FIELD

The embodiments discussed herein are related to a resist composition and a method for forming a pattern.

BACKGROUND

Inorganic materials, such as silicon oxide (SiO), silicon nitride (SiN), and phosphorus-added silicon oxide (PSG), and fluorine-added silicon oxide (SiOF), and organic materials, such as polyimide, are known as materials for insulating films used in electronic devices, such as semiconductor devices. As a method for forming an insulating film, for example, a method in which a chemical vapor deposition (CVD) method is employed, a method in which a polymerization of a silicon-containing compound is employed, and a method in which a resin material to be formed into an insulating film is applied are known.

Japanese Laid-open Patent Publication Nos. 2010-056156, 2006-278506, and 2012-053243 are examples of related art.

In the case where heat treatment is performed when an insulating film is formed, a conductive portion, such as wiring, may be broken because of heat stress, and a material used in the conductive portion may be diffused, depending on the temperature.

There is a method that includes forming an insulating film, forming a resist pattern, forming an opening portion in the insulating film by etching with the resist pattern serving as a mask, and forming a conductive portion, such as wiring, in the formed opening portion. In this method, the opening portion in the insulating film and an underlying layer may be damaged by etching, and variations in the size of the opening portion may occur.

SUMMARY

According to an aspect of the invention, a resist composition includes: a solvent; and a resin in the solvent, the resin being prepared by the hydrolysis and condensation of an alkoxy group-containing compound that contains an alkoxy group bound to a silicon atom or a germanium atom in the presence of an acid or an alkali, wherein a portion of the resist composition irradiated with an energy radiation is insoluble in a developing solution.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

A resist composition contains a resin in a solvent, the resin being prepared by the hydrolysis and condensation of an alkoxy group-containing compound that contains an alkoxy group bound to a silicon atom or a germanium atom in the presence of an acid or an alkali. The resist composition is a negative-type resist composition, in which a portion of the resist composition irradiated with an energy radiation is insoluble in a developing solution.

Here, the alkoxy group-containing compound is represented by formula (1):

$$R^1_{4-n}M(OR^2)_n \qquad (1)$$

where in formula (1), M represents a silicon (Si) atom or a germanium (Ge) atom; n represents an integer of 1 to 4; $R^1$ represents a hydrogen atom, a fluorine atom, an alkyl group having 1 to 8 carbon atoms, a vinyl group, an alicyclic group, an aryl group, or a derivative thereof, and when n represents 2 or less, $R^1$'s may be the same or different; $R^2$ represents a hydrogen atom, an alkyl group having 1 to 8 carbon atoms, an allyl group, a vinyl group, or an alicyclic group, and when n represents 2 or more, $R^2$'s may be the same or different.

The resin contained in the resist composition is prepared by the hydrolysis and condensation of one or more alkoxy group-containing compounds represented by formula (1) in the presence of an acid or an alkali.

Examples of the alkoxy group-containing compound (silane compound) in which M in formula (1) represents a silicon atom include tetraalkoxysilane, trialkoxysilane, methyltrialkoxysilane, ethyltrialkoxysilane, propyltrialkoxysilane, phenyltrialkoxysilane, vinyltrialkoxysilane, allyltrialkoxysilane, glycidyltrialkoxysilane, dialkoxysilane, dimethyldialkoxysilane, diethyldialkoxysilane, dipropyldialkoxysilane, diphenyldialkoxysilane, divinyldialkoxysilane, diallyldialkoxysilane, diglycidyldialkoxysilane, phenylmethyldialkoxysilane, phenylethyldialkoxysilane, phenylpropyltrialkoxysilane, phenylvinyldialkoxysilane, phenylallyldialkoxysilane, phenylglycidyldialkoxysilane, methylvinyldialkoxysilane, ethylvinyldialkoxysilane, and propylvinyldialkoxysilane; a compound in which a hydrogen atom of a group, corresponding to $R^1$ in formula (1), in each of the foregoing silane compounds is replaced with a fluorine atom; and a compound in which a predetermined hydrogen atom of an alkyl group, a vinyl group, an alicyclic group, or an aryl group, corresponding to $R^1$ in formula (1), in each of the foregoing silane compounds is replaced with another group (for example, an aryl group or a group containing an ester bond or an ether bond).

Examples of the alkoxy group-containing compound (germane compound) in which M in formula (1) represents a germanium atom include compounds in which silicon atoms in the foregoing silane compounds are replaced with germanium atoms, that is, tetraalkoxygermane, trialkoxygermane, methyltrialkoxygermane, ethyltrialkoxygermane, propyltrialkoxygermane, phenyltrialkoxygermane, vinyltrialkoxygermane, allyltrialkoxygermane, glycidyltrialkoxygermane, dialkoxygermane, dimethyldialkoxygermane, diethyldialkoxygermane, dipropyldialkoxygermane, diphenyldialkoxygermane, divinyldialkoxygermane, diallyldialkoxygermane, diglycidyldialkoxygermane, phenylmethyldialkoxygermane, phenylethyldialkoxygermane, phenylpropyltrialkoxygermane, phenylvinyldialkoxygermane, phenylallyldialkoxygermane, phenylglycidyldialkoxygermane, methylvinyldialkoxygermane, ethylvinyldialkoxygermane, and propylvinyldialkoxygermane; a compound in which a hydrogen atom of a group, corresponding to $R^1$ in formula (1), in each of the foregoing germane compounds is replaced with a fluorine atom; and a compound in which a predetermined hydrogen atom of an alkyl group, a vinyl group, an alicyclic group, or an aryl group, corresponding to $R^1$ in formula (1), in each of the foregoing germane compounds is replaced with another group (for example, an aryl group or a group containing an ester bond or an ether bond).

The resin (prepared from one or more alkoxy group-containing compounds as described above) contained in the resist composition preferably has a weight-average molecular weight (Mw) of 500 to 50,000,000 and more preferably 7,000 to 48,000,000. A weight-average molecular weight of less than 500 may result in a reduction in the boiling point of the resin to cause the cleavage of the resin backbone and the evaporation of a cleaved component during heat treatment mainly for the purpose of drying the solvent as described below. A weight-average molecular weight of more than 50,000,000 may result in a reduction in solubility (or dilution property) in the solvent.

The resist composition preferably has a resin content of 10% by mass to 70% by mass and more preferably 20% by mass to 60% by mass.

The solvent contained in the resist composition is not particularly limited as long as the resin is dissolved therein. Examples of the solvent include cyclohexanone, methyl isobutyl ketone, methyl ethyl ketone, methyl cellosolve, ethyl cellosolve, octane, decane, propylene glycol, propylene glycol monomethyl ether, propylene glycol monomethyl ether acetate, diethylene glycol, propylene glycol monoethyl ether, and propylene glycol monopropyl ether.

For example, a silicone compound having a backbone containing a hydrocarbon may be added to the resist composition containing the resin and the solvent described above in order to improve chemical resistance to, for example, acids and bases, and moisture resistance. Examples of the additive compound include polydimethylcarbosilane, polyhydromethylcarbosilane, polydiethylcarbosilane, polyhydroethylcarbosilane, polycarbosilastyrene, polyphenylmethylcarbosilane, polydiphenylcarbosilane, polydimethylsilphenylenesiloxane, polymethylsilphenylenesiloxane, polydiethylsilphenylenesiloxane, polyethylsilphenylenesiloxane, polydipropylsilphenylenesiloxane, polypropylsilphenylenesiloxane, polyphenylsilphenylenesiloxane, polydiphenylsilphenylenesiloxane, polyphenylmethylsilphenylenesiloxane, polyphenylethylsilphenylenesiloxane, polyphenylpropylsilphenylenesiloxane, polyethylmethylsilphenylenesiloxane, polymethylpropylsilphenylenesiloxane, and polyethylpropylsilphenylenesiloxane.

The amount of the additive compound added is preferably 0.1 parts by weight to 200 parts by weight with respect to 100 parts by weight of the resin in the resist composition. When the amount of the additive compound added is less than 0.1 parts by weight, the effects of the chemical resistance and the moisture resistance are not provided, in some cases. When the amount of the additive compound added is more than 200 parts by weight, the mechanical strength of an insulating film formed from the resist composition, as described below, is reduced, in some cases.

A method for preparing the resist composition is not particularly limited. The resist composition may be prepared by, for example, dissolving a silane compound or germane compound as described above in a solvent (as described above) and then allowing hydrolysis as illustrated in formula (1A) and condensation as illustrated in formulae (2A) and (2B) to proceed.

(1A)

(2A)

(2B)

In the hydrolysis and condensation, a catalyst of an acid or alkali, for example, a strong acid or strong alkali is used. As the catalyst, an organic acid or organic alkali may be used. As the organic acid or organic alkali, for example, a compound containing, in its molecule, at least one hydrocarbon selected from aliphatic, alicyclic, and aromatic hydrocarbons is used. Examples of the organic acid compound include maleic acid, acetic acid, sulfonic acid, and toluenesulfonic acid. These compounds may be used separately or in combination of two or more thereof. Examples of the organic alkali compound include pyridine, triethylamine, and tetraalkylammonium hydroxide (TAAOH). These compounds may be used separately or in combination of two or more thereof.

Examples of tetraalkylammonium hydroxide include tetramethylammonium hydroxide, tetraethylammonium hydroxide, tetrapropylammonium hydroxide, tetrabutylammonium hydroxide, tetra-n-octylammonium hydroxide, n-hexadecyltrimethylammonium hydroxide, and n-octadecyltrimethylammonium hydroxide. These compounds may be used separately or in combination of two or more thereof.

As illustrated in formula (1A), a molecule having an alkoxy group at an end (a monomer or polymer of a silane compound or germane compound) is hydrolyzed in the solvent in the presence of an acid or alkali to form an alcohol and a molecule having a silanol group at an end. As illustrated in formula (2A), molecules each having a silanol group at an end are condensed in the solvent to form water and a resin having an atom M-containing backbone serving as either or both the main and side chains. As illustrated in formula (2B), a molecule having a silanol group at an end and a molecule having an alkoxy group at an end are condensed in the solvent to form an alcohol and a resin having an atom M-containing backbone serving as either or both main and side chains.

The hydrolysis and condensation proceed to form the resin having an atom M-containing backbone in the solvent. Examples of the resulting resin may include a resin having a molecular structure in which an atom M-containing backbone extends linearly; a resin having a molecular structure in which an atom M-containing backbone extends three-dimensionally; and a resin having a cage-like molecular structure. A resin having a molecular structure that extends in such a manner that molecular chains are entangled, a resin having a molecular structure that extends three-dimensionally, and a resin having a cage-like molecular structure are formed in the solvent separately or in combination as a mixture thereof, depending on hydrolysis and condensation conditions (for example, the types and amounts of monomer, solvent, and catalyst). The resulting resin forms a plurality of clusters in the solvent. The solvent, the catalyst, the alcohol generated by the hydrolysis and condensation, and so forth are contained between the resin clusters.

The resist composition may be prepared by such a method as described above. The resin content of the resist composition may be adjusted by removing certain amounts of the solvent, the alcohol, and so forth from the resulting resist composition or adding the solvent.

Figure 1:
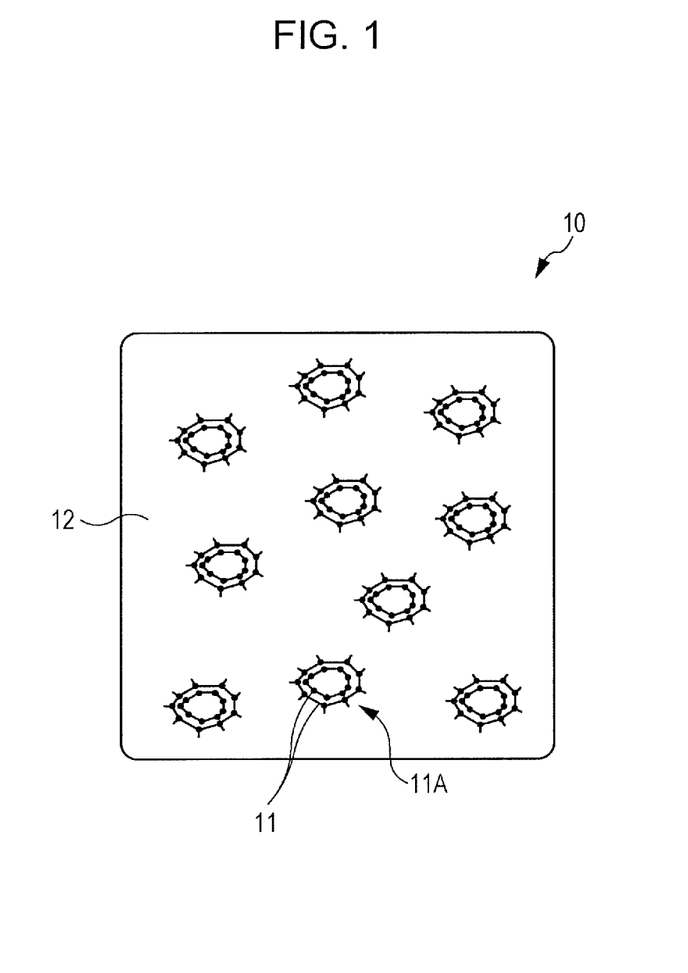
FIG. 1 is a schematic drawing of an example of a resist composition.

FIG. 1 is a schematic drawing of an example of a resist composition.

A resist composition 10 illustrated in FIG. 1 contains clusters 11A of a resin 11 and a solvent 12. Here, a state in which the clusters 11A of the resin 11 having a cage-like molecular structure are dispersed in the solvent 12 is schematically illustrated as an example. Examples of the dispersion state of the clusters 11A include a state in which the clusters are individually dispersed in the solvent 12 as illustrated in FIG. 1; and a state in which aggregates of the plural clusters are dispersed in the solvent 12.

A catalyst that has been used to form the resin 11 is contained in the solvent 12 in addition to the clusters 11A of the resin 11. The catalyst is composed of an acid or alkali. Hydrolysis and condensation of the silane compound or germane compound in the presence of the catalyst result in the formation of the resin 11 and the clusters 11A. The hydrolysis and condensation occur partially in the solvent 12 to form the resin 11 and the clusters 11A without gelation of the resist composition 10.

A method for forming an insulating film with a resist composition as described above will be described below.

Figure 2:
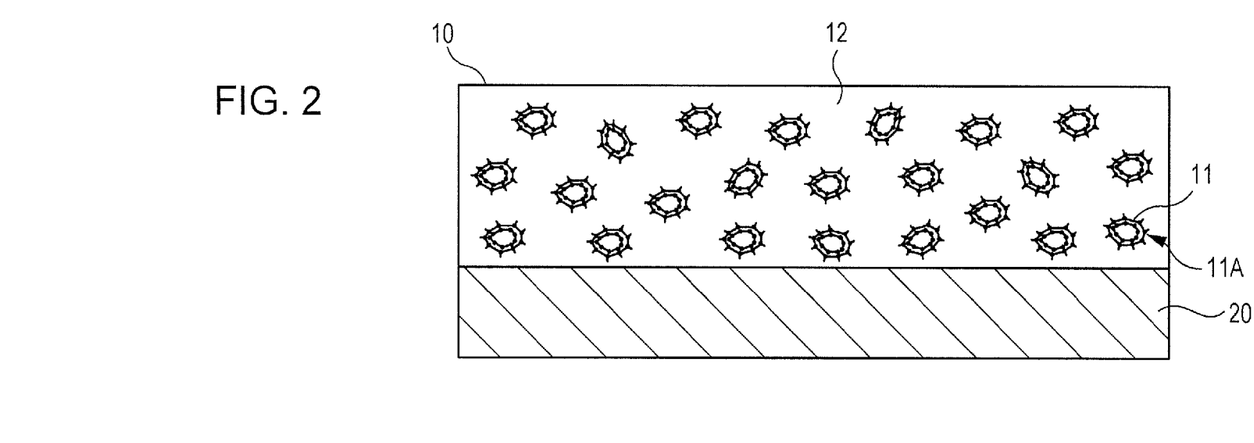
FIG. 2 is a schematic drawing of an example of a step of applying a resist composition.

FIG. 2 is a schematic drawing of an example of a step of applying a resist composition.

As illustrated in FIG. 2, the resist composition 10 is provided on a substrate 20. The resist composition 10 is provided on the substrate 20 by a coating method. The resist composition 10 is prepared so as to exhibit a certain level of flowability without gelation. It is thus possible to provide the resist composition 10 on the substrate 20 by the coating method.

The resist composition 10 may be applied by, for example, a spin-coating method, a dip-coating method, a kneader coating method, a curtain coating method, or a blade coating method. From the viewpoint of achieving good coating efficiency, the spin-coating method and the dip-coating method are preferred.

The type of the substrate 20 to which the resist composition 10 is applied is not particularly limited. For example, in the field of the production of semiconductor devices, the substrate 20 may be a semiconductor substrate or a compound semiconductor substrate. Alternatively, the substrate 20 may be a substrate in which a semiconductor layer or a compound semiconductor layer is formed on a surface layer portion of a semiconductor substrate or a compound semiconductor substrate. Furthermore, the substrate 20 may be a substrate including an insulating film, such as an interlayer insulator, and the resist composition 10 may be provided on the insulating film. Moreover, the substrate 20 may be an insulating substrate.

After the application of the resist composition 10 on the substrate 20 as described above, heat treatment, irradiation with an energy radiation, and development are performed.

Figure 3:
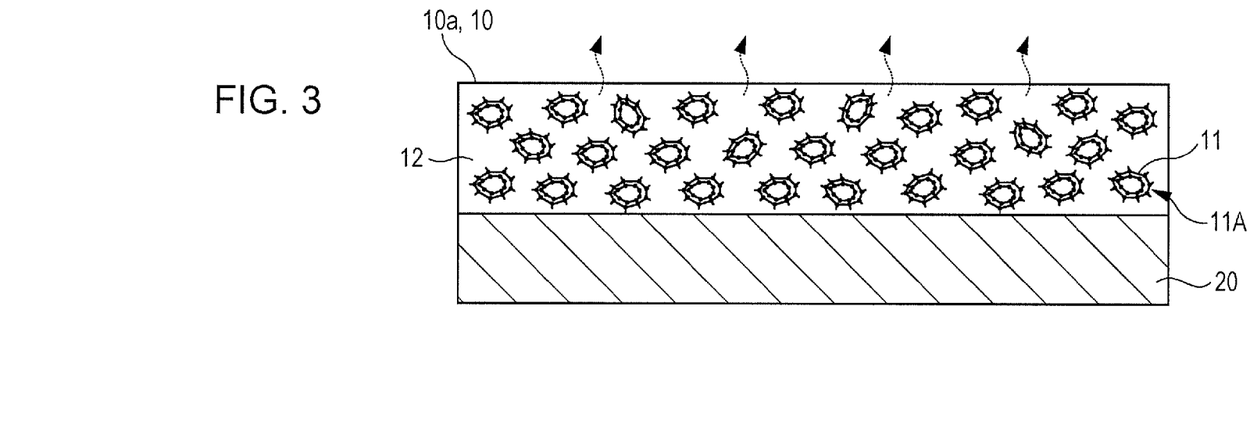
FIG. 3 is a schematic drawing of an example of a heat-treatment step.

FIG. 3 is a schematic drawing of an example of a heat-treatment step.

After the application of the resist composition 10 on the substrate 20, heat treatment (prebake) is performed. The heat treatment aims mainly to evaporate the solvent 12 in the resist composition 10 applied to the substrate 20. In this heat treatment, the solvent 12 in the resist composition 10 may not be completely evaporated. The heat treatment temperature is preferably 50° C. to 300° C. and more preferably 100° C. to 250° C. The heat treatment results in the evaporation of the solvent 12 (indicated by dotted arrows in FIG. 3) from a surface of the resin 11 and portions between the clusters 11A in the resist composition 10, thereby forming a resist 10a (the resist composition 10) on the substrate 20.

The evaporation of the solvent 12 by the heat treatment may cause the volume of the resist 10a on the substrate 20 to decrease. During the heat treatment, the rearrangement and aggregation of the resin 11 and the clusters 11A may occur, and the bonding of the resin 11 and the clusters 11A may be formed by the action of the catalyst in the solvent 12 (hydrolysis and condensation).

Figure 4:
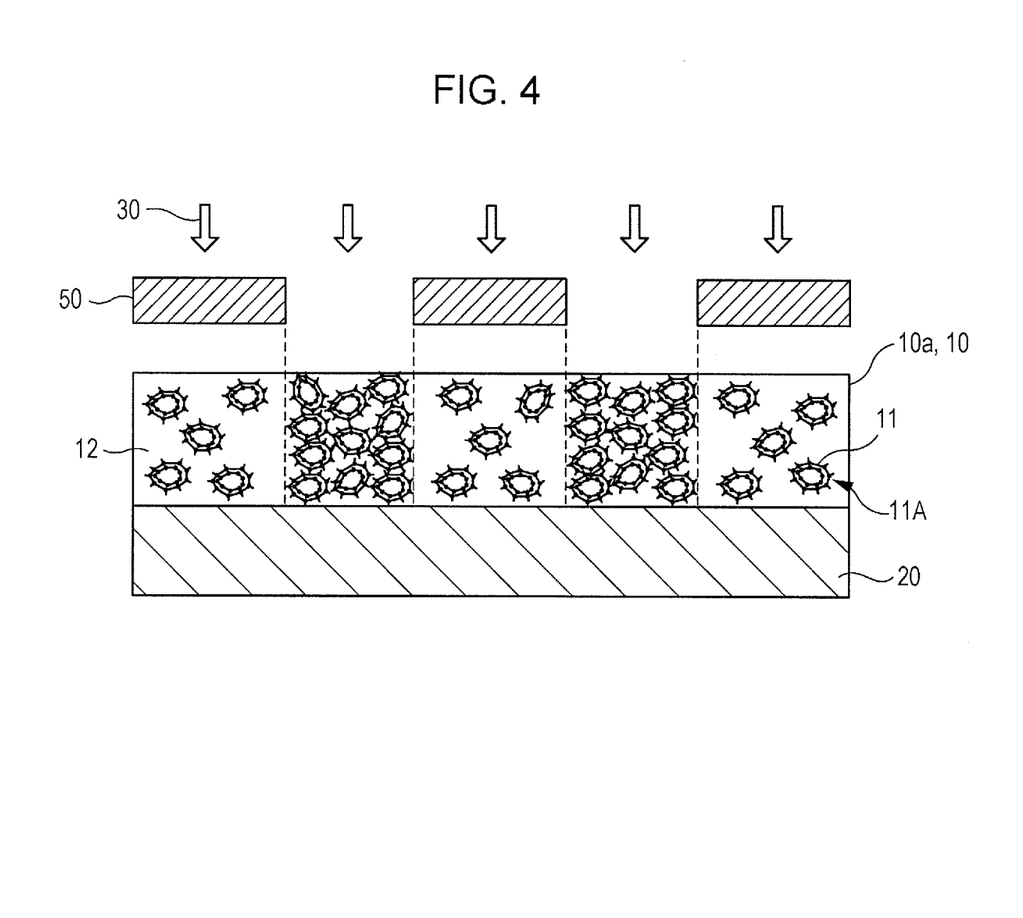
FIG. 4 is a schematic drawing of an example of a step of irradiation with an energy radiation.

FIG. 4 is a schematic drawing of an example of a step of irradiation with an energy radiation.

After the formation of the resist 10a on the substrate 20 by the heat treatment, a predetermined portion of the resist 10a is selectively irradiated with an energy radiation 30 using a mask 50 as illustrated in FIG. 4. Examples of the energy radiation 30 with which the resist 10a is irradiated include infrared radiation, visible radiation, ultraviolet radiation, excimer laser beams, X-rays, and electron beams.

When the predetermined portion of the resist 10a is irradiated with the energy radiation 30, the evaporation of the solvent 12 proceeds in the irradiated portion of the resist 10a. Simultaneously, at the portion irradiated with the energy radiation 30, for example, the action of the remaining catalyst allows the hydrolysis and condensation as illustrated in formulae (1A), (2A), and (2B) to proceed between the clusters 11A of the resin 11. The evaporation of the solvent 12 by irradiation with the energy radiation 30 and the progression of the hydrolysis and condensation of the clusters 11A result in the curing (gelation) of the portion of the resist 10a irradiated with the energy radiation 30, thereby forming a latent image pattern.

The cured portion of the resist 10a of the latent image pattern is not dissolved (negative) in a predetermined developing solution. At the cured portion of the resist 10a, the evaporation of the solvent 12 and so forth by irradiation with the energy radiation 30 and the progression of the hydrolysis and condensation of the resin 11 and the clusters 11A result in the formation of a three-dimensional network structure of the resin 11. Gaps in the three-dimensional network structure are formed as voids.

To promote the hydrolysis and condensation of the clusters 11A in the resist 10a, an active energy radiation, for example, ultraviolet radiation, an excimer laser beam, X-rays, or an electron beam, is preferably used as the energy radiation 30. In the case of using ultraviolet radiation, ultraviolet radiation with a wavelength of 450 nm or less is preferred. In the case of using an excimer laser beam, for example, krypton fluoride (KrF) excimer laser light (wavelength: 248 nm), argon fluoride (ArF) excimer laser light (wavelength: 193 nm), or fluorine ($F_2$) excimer laser light (wavelength: 157 nm) is preferred.

To promote and uniformize the hydrolysis and condensation of the clusters 11A in the resist 10a, additional heat treatment may be performed after the irradiation with the energy radiation 30.

While the case where the predetermined portion of the resist 10a is selectively irradiated with the energy radiation 30 is exemplified here, the entire resist 10a may be irradiated with the energy radiation 30 to entirely cure the resist 10a.

Figure 5:
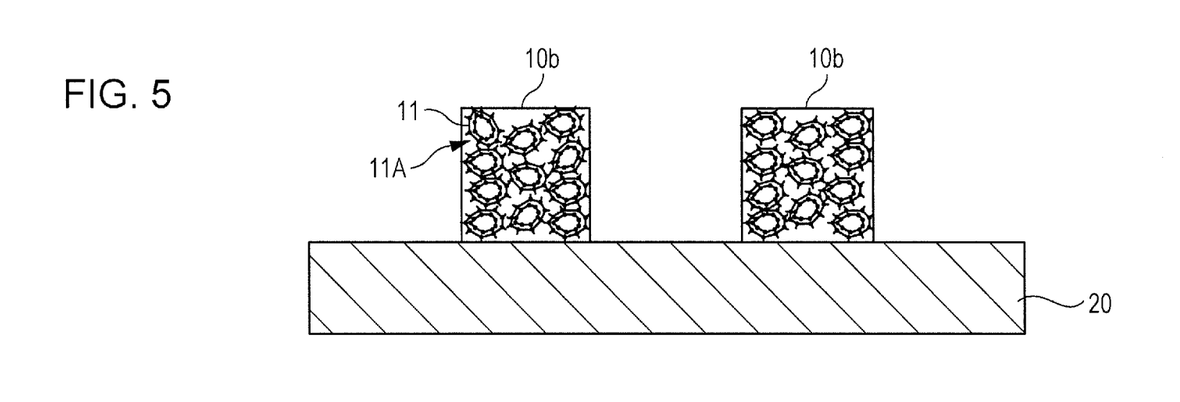
FIG. 5 is a schematic drawing of an example of a development step.

FIG. 5 is a schematic drawing of an example of a development step.

After the resist 10a on the substrate 20 is irradiated with the energy radiation 30, developing is performed by dissolving and removing a portion that is not irradiated with the energy radiation 30 (an uncured portion of the resist 10a) using the predetermined developing solution from the substrate 20.

The type of developing solution is not particularly limited as long as the uncured portion of the resist 10a is dissolved in the developing solution. Examples of the developing solution that may be used include the solvent 12 used in the resist composition 10; water; and aqueous solutions of alkalis.

Examples of alkalis used for the developing solution include inorganic alkalis, such as sodium hydroxide, potassium hydroxide, sodium silicate, and ammonia; primary amines, such as ethylamine and propylamine; secondary amines, such as diethylamine and dipropylamine; tertiary amines, such as trimethylamine and triethylamine; alcohol amines, such as diethylethanolamine and triethanolamine; and quaternary ammonium hydroxides, such as tetramethylammonium hydroxide, tetraethylammonium hydroxide, tetrabutylammonium hydroxide, triethylhydroxymethylammonium hydroxide, and trimethylhydroxyethylammonium hydroxide.

The aqueous solution of an alkali may further contain an additive. Examples of the additive include water-miscible organic solvents, such as methyl alcohol, ethyl alcohol, propyl alcohol, and ethylene glycol; surfactants; and agents to inhibit the dissolution of the resin 11.

As described above, the dissolution and removal of the uncured portion (the portion that is not irradiated with the energy radiation 30) of the resist 10a with the predetermined developing solution result in the formation of a resist pattern (insulating film pattern) 10b containing voids on the substrate 20.

For example, a conductive portion may be formed on the resulting insulating film pattern 10b.

Figure 6:
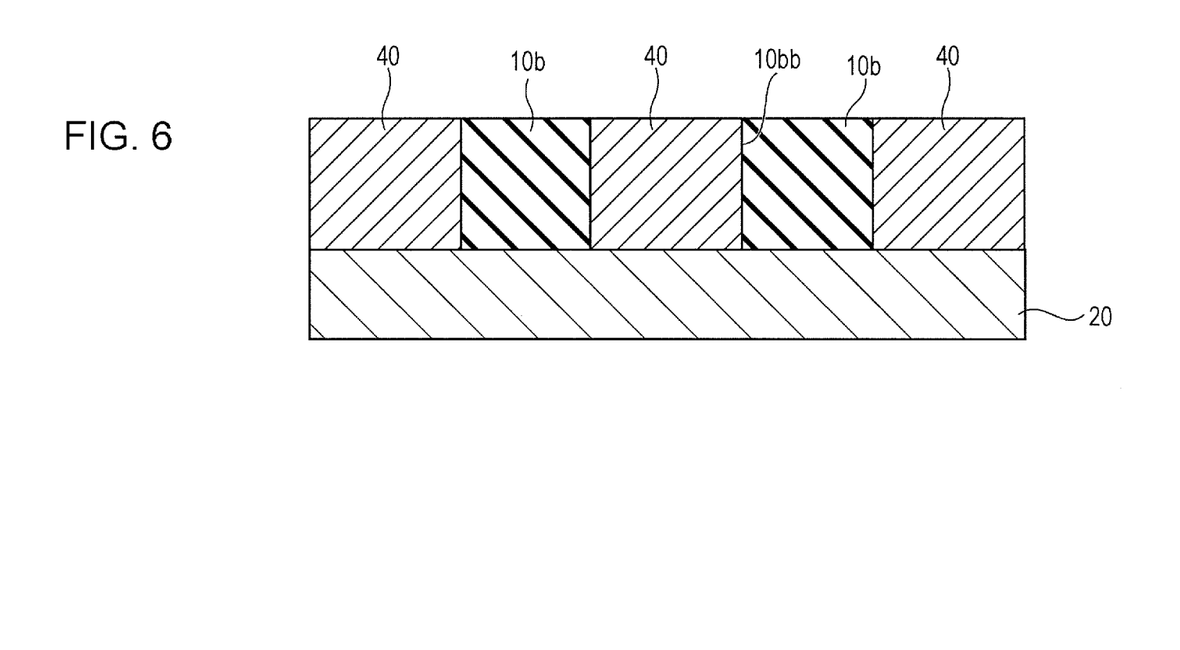
FIG. 6 is a schematic drawing of an example of a step of forming a conductive portion.

FIG. 6 is a schematic drawing of an example of a step of forming a conductive portion.

In the case where the insulating film pattern 10b is used as an insulating film (interlayer insulator) for a semiconductor device, a conductive portion 40, for example, an electrode or wiring, may be formed in a recessed portion 10bb (a portion formed by the dissolution and removal with the developing solution) of the insulating film pattern 10b. The conductive portion 40 may be formed by any of a variety of methods, such as a sputtering method, a plating method, and a chemical vapor deposition (CVD) method.

The insulating film pattern 10b contains the voids and thus has a low dielectric constant.

For example, in the field of semiconductors, there have been advances in the miniaturization of semiconductor devices and higher density of lines. Narrow spaced lines result in high capacitance between the lines, thus possibly causing wiring delay. Here, the relationship among wiring delay T, wiring resistance R, and capacitance C between lines is expressed by formula (3). Capacitance C is expressed by formula (4).

$$T \propto C \times R \tag{3}$$

$$C = \in_0 \times \in_r \times S/d \tag{4}$$

where in formula (4), S represents the area of facing lines, $\in_0$ represents the dielectric constant of vacuum, $\in_r$ represents the dielectric constant of the insulating film, and d represents a distance between the lines. Formulae (3) and (4) state that a method for effectively reducing wiring delay is to reduce the dielectric constant of the insulating film.

Inorganic films, such as silicon oxide films and silicon nitride films, are well known as insulating films for use in semiconductor devices. These inorganic films have relatively high dielectric constants. Thus, a technique for reducing a dielectric constant by forming a porous insulating film with a resin material is also known.

An example of a method for forming such a porous insulating film is a method that includes applying a resin material (for example, a siloxane-based resin) that contains a template (for example, a pyrolytic organic resin) on a substrate, polymerizing the resin material, and decomposing and removing the template by heating. In the method for forming a porous insulating film, however, the decomposition may be performed at 300° C. to 500° C., depending on the type of substance used for the template. In this case, thermal stress is applied to a conductive portion, such as wiring, that has been formed before the formation of the porous insulating film, thereby possibly causing a break of the conductive portion. Furthermore, a material, such as a metal, used in the conductive portion may be diffused into the insulating film. Thus, the performance, reliability, and production stability of a semiconductor device may be reduced.

In the case where in a production process of a semiconductor device, an insulating film is formed by the foregoing method for forming a porous insulating film with a template and where a conductive portion, such as wiring, is formed on the resulting insulating film, a photolithography technique and an etching technique are employed. That is, after a porous insulating film is formed on a base, for example, a semiconductor substrate or an insulating film, a resist pattern is formed on the porous insulating film. The porous insulating film is etched using the resist pattern as a mask. A conductive portion is formed in a recessed portion of the porous insulating film formed by etching. However, when the porous insulating film is etched using the resist pattern as a mask, the porous insulating film or the base around the recessed portion are damaged, and an increase and variations in the size of the recessed portion occur. Thus, the performance, reliability, and production stability of a semiconductor device may be reduced. Furthermore, in such a process, the costs of the formation of the pattern of the porous insulating film and the production of the semiconductor device may be increased.

In the case of employing the foregoing method for forming a porous insulating film with a template, a path taken by decomposition and removal of the template may be formed into a void. In this case, a large-sized void or a long serially-connected void may be formed in the porous insulating film. The formation of such a void may lead to a reduction in the mechanical strength of the porous insulating film and cause a material of the conductive portion formed in the porous insulating film to be diffused. Thus, the performance, reliability, and production stability of a semiconductor device may be reduced.

In contrast, in the foregoing method for forming the insulating film pattern 10b, the resist composition 10 formed on the substrate 20 is not subjected to heat treatment at a relatively high temperature such that the template is decomposed and removed, but subjected to heat treatment at a relatively low temperature such that the solvent 12 in the resist composition 10 is evaporated. It is thus possible to inhibit the occurrence of a break of the conductive portion, such as wiring, and the diffusion of the material of the conductive portion during the formation of the insulating film pattern 10b.

Furthermore, in the foregoing method for forming the insulating film pattern 10b, etching is not performed. That is, the latent image pattern insoluble in the developing solution is formed by irradiation with the energy radiation 30, and the insulating film pattern 10b is formed by developing. Etching may cause damage to the insulating film pattern and the base and the occurrence of variations in the insulating film pattern. In the method for forming the insulating film pattern 10b, damage to the insulating film pattern and the base and the occurrence of variations in the insulating film pattern are inhibited. Furthermore, a step of separately forming a resist pattern on the insulating film and a step of performing etching using the resist pattern as a mask are not performed. It is thus possible to reduce the number of steps of forming the insulating film pattern and the semiconductor device, thereby reducing the production cost.

In the foregoing method for forming the insulating film pattern 10b, the resin 11 and the clusters 11A are formed and bound together to form the three-dimensional network structure of the resin 11 in the insulating film pattern 10b, and the solvent 12 is removed to form the voids. Thus, compared with the method for forming a porous insulating film with a template, the method including decomposing and removing the template, the formation of a large-sized void and a long serially-connected void is inhibited. Therefore, it is possible to form the insulating film pattern 10b containing uniform small-sized voids and having high mechanical strength.

In the foregoing method for forming the insulating film pattern 10b, it is possible to efficiently form the insulating film pattern 10b containing the voids and having a low dielectric constant at low cost. Furthermore, by employing the foregoing method for forming the insulating film pattern 10b, it is possible to stably produce a high-performance semiconductor device with high reliability.

The formation of the insulating film pattern 10b from the resist composition 10 has been described above.

Here, the size and density of the voids formed in the insulating film pattern 10b may be adjusted by, for example, the type (molecular structure and combination) of the alkoxy group-containing compound which is represented by formula (1) and which is used for the resist composition 10 and by the types and amounts of solvent and catalyst. The size (average void size) of the voids in the insulating film pattern 10b is not particularly limited and may be appropriately selected, depending on the application of the insulating film pattern 10b. For example, in the case where the insulating film pattern 10b is formed in a semiconductor device, the voids preferably have a size of 10 nm or less and more preferably 8 nm or less from the viewpoint of achieving a low dielectric constant. The size of the voids may be observed and measured with, for example, a transmission electron microscope (TEM).

The thickness of the insulating film pattern 10b is not particularly limited and may be appropriately selected, depending on the application of the insulating film pattern 10b. The insulating film pattern 10b preferably has a thickness of about 20 nm to about 3000 nm from the viewpoint of achieving the formation of the insulating film pattern 10b which contains the voids and which has a low dielectric constant and good uniformity.

The resist composition 10 used for the formation of the insulating film pattern 10b contains the catalyst which acts on the formation of the resin 11 and the clusters 11A through the hydrolysis and condensation of the alkoxy group-containing compound and on the bonding of the resin 11 and the clusters 11A by irradiation with the energy radiation 30. The use of the foregoing organic acid or organic alkali as the catalyst may inhibit the occurrence of the defective molecular structure (nonuniformity) of the resin 11 when the insulating film pattern 10b is formed (by irradiation with the energy radiation 30 and the curing of the resist 10a). In the case where the organic alkali is used as the catalyst, when the insulating film pattern 10b is formed (by irradiation with the energy radiation 30 and the curing of the resist 10a), molecules of the resin 11 having a high density are formed, compared with the organic acid, thereby improving the mechanical strength.

Examples of the catalyst that may be used include inorganic acids, such as nitric acid, hydrochloric acid, and sulfuric acid, in addition to the organic acid and organic alkali.

The resin 11, which is used for the formation of the insulating film pattern 10b, in the resist composition 10 and the resist 10a that is formed from the resist composition 10 has the main backbone containing a silicon atom or germanium atom. In the case where the energy radiation 30 with which the resist 10a is irradiated is an electron beam, the sensitivity to the electron beam depends on the amount of secondary electrons generated in the resist 10a. Thus, in the case where the energy radiation 30 is the electron beam, in the resin 11 having a main backbone containing a germanium atom, that is, in the resist 10a and the resist composition 10 containing the resin 11 prepared by the use of a germane compound, it is possible to achieve higher sensitivity to the electron beam.

In the case where the electron beam is used as the energy radiation 30, the use of the alkoxy group-containing compound represented by formula (1), $R^1$ representing an aryl group or a group containing a derivative thereof, may improve the sensitivity to the electron beam. For example, in formula (1), $R^1$ represents a group obtained by removing at least one hydrogen atom from benzene, naphthalene, anthracene, phenanthrene, triphenylene, pyrene, chrysene, or naphthacene. Specifically, $R^1$ represents a 1-naphthyl group, 2-naphthyl group, 1-anthracenyl group, 2-anthracenyl group, 1-phenanthryl group, 2-phenanthryl group, 3-phenanthryl group, 1-pyrenyl group, or the like. When the alkoxy group-containing compound having $R^1$ that represents an aryl group is used as the whole or part of an alkoxy group-containing compound used to form the resist composition 10, it is possible to form the resist composition 10 and the resist 10a having high sensitivity to the electron beam.

However, in the case where the alkoxy group-containing compound having $R^1$ that represents an aryl group in formula (1) is used as the whole of an alkoxy group-containing compound used to form the resist composition 10, the number of voids formed in the insulating film pattern 10b may be relatively small. In such a case, an alkoxy group-containing compound having $R^1$ that represents an organic functional group, for example, an alkyl group, a vinyl group, or an alicyclic group, is added to the alkoxy group-containing compound having $R^1$ that represents an aryl group in formula (1). Alternatively, an alkoxy group-containing compound that is a tetrafunctional compound having four alkoxy groups $OR^2$'s (n=4) is added to the alkoxy group-containing compound having $R^1$ that represents an aryl group. In an alternative way, an alkoxy group-containing compound having $R^1$ that represents an organic functional group, such as an alkyl group, and an alkoxy group-containing compound that is a tetrafunctional compound having four alkoxy groups $OR^2$'s (n=4) are both added to the alkoxy group-containing compound having $R^1$ that represents an aryl group. As described above, when such a different alkoxy group-containing compound is added to the alkoxy group-containing compound which has $R^1$ that represents an aryl group and which has high sensitivity to the electron beam, a copolymer thereof is formed in the resist composition 10 and the resist 10a, thereby promoting the formation of the voids. Furthermore, the use of such plural alkoxy group-containing compounds inhibits the volumetric shrinkage of the resist 10a due to the electron beam irradiation.

A compound having a decomposable group that is decomposed (cleaved) by the application of a predetermined amount of energy may be used as the alkoxy group-containing compound used for the resist composition 10. For example, an alkoxy group-containing compound having a decomposable group by heating to a temperature of 150° C. to 350° C. or irradiation with the energy radiation 30 is used. For example, in formula (1), $R^1$ that represents a functional group containing an ester linkage, an ether linkage, or any combination thereof is preferably used as the decomposable group. The use of the alkoxy group-containing compound having such a decomposable group results in the formation of the resin 11 having the decomposable group in the resist composition 10. The decomposable group is decomposed by heating to a predetermined temperature or irradiation with the energy radiation 30. An end of the resin 11 in which the decomposable group has been decomposed serves as a new reactive site to allow polymerization to proceed, thereby forming the voids and improving the density of the film. The use of the decomposable group having a decomposition temperature of less than 150° C. may not provide the effect of sufficiently forming the voids by the incorporation of the decomposable group. When the decomposable group has a decomposition temperature of more than 350° C., the gelation of the resist 10a may proceed to cause difficulty in forming the voids, and the backbone of the resin 11 may be significantly deformed.

Examples including the preparation of resist compositions as described above and the formation of insulating film patterns from the resist compositions will be described below.

Example 1

To a 200-mL reaction vessel, 20.8 g (0.1 mol) of tetraethoxysilane, 17.8 g (0.1 mol) of methyltriethoxysilane, 24.8 g (0.1 mol) of 1-naphthyltrimethoxysilane, and 40 g of methyl isobutyl ketone were charged. To the reaction vessel, 16.2 g (0.9 mol) of an aqueous solution of 400 ppm nitric acid was added dropwise over a period of 10 minutes. After the completion of the dropwise addition, an aging reaction was performed for 2 hours. Next, 5 g of magnesium sulfate was added thereto to remove an excess of water. Then ethanol formed by the aging reaction was removed with a rotatory evaporator until the amount of the reaction solution was reduced to 50 mL. To the resulting reaction solution, 20 mL of methyl isobutyl ketone was added. Methyl isobutyl ketone was removed with an oven at 200° C., thereby preparing a resist composition having a solid concentration of 17.0% by weight.

Example 2

To a 200-mL reaction vessel, 25.3 g (0.1 mol) of tetraethoxygermane, 22.3 g (0.1 mol) of methyltriethoxygermane, 24.8 g of (0.1 mol) of 1-naphthyltrimethoxysilane, and 40 g of methyl isobutyl ketone were charged. To the reaction vessel, 16.2 g (0.9 mol) of an aqueous solution of 1% tetramethylammonium hydroxide was added dropwise over a period of 10 minutes. After the completion of the dropwise addition, an aging reaction was performed for 2 hours. Next, 5 g of magnesium sulfate was added thereto to remove an excess of water. Then ethanol formed by the aging reaction was removed with a rotatory evaporator until the amount of the reaction solution was reduced to 50 mL. To the resulting reaction solution, 20 mL of methyl isobutyl ketone was added. Methyl isobutyl ketone was removed with an oven at 200° C., thereby preparing a resist composition having a solid concentration of 16.1% by weight.

Example 3

Each of the resist compositions prepared in Examples 1 and 2 was applied to a silicon wafer by a spin-coating method (at 2000 rpm for 30 seconds) and then subjected to heat treatment at 150° C. A pattern 10 mm on a side and fine lines were exposed with an electron beam exposure apparatus at an acceleration voltage of 50 keV. A portion other than an exposed portion was removed (developed) with an aqueous solution of tetramethylammonium hydroxide. A gold electrode having a diameter of 1 mm was formed on the resulting insulating film pattern. The dielectric constant was measured. The average size of voids was measured with a TEM. Table describes the sensitivity to the electron beam ($mC/cm^2$), the resolution (nm), the dielectric constant, and the average void size (nm).

TABLE

|  | Example 1 | Example 2 |
|---|---|---|
| Sensitivity ($mC/cm^2$) | 0.85 | 0.72 |
| Resolution (nm) | 50 | 50 |
| Dielectric constant | 2.12 | 2.26 |
| Average void size (nm) | 6.6 | 7.5 |

As is clear from Table, by employing the foregoing method, the resist compositions each having high sensitivity and high resolution were prepared, and the insulating film patterns each having a small average void diameter and a low dielectric constant were formed.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:
1. A resist composition comprising:
   a solvent; and
   a resin in the solvent, the resin being prepared by the hydrolysis and condensation of an alkoxy group-containing compound that contains an alkoxy group bound to a silicon atom or a germanium atom in the presence of an acid or an alkali,
   wherein the resin is in a form of clusters dispersed in the solvent.
2. The resist composition according to claim 1,
   wherein the alkoxy group-containing compound is represented by the following formula, and the resin is prepared by the hydrolysis and condensation of at least one type of the alkoxy group-containing compound, $$R^1{}_{4-n}M^1(OR^2)_n \qquad (1)$$

where in formula (1), $M^1$ represents a silicon atom or a germanium atom; n represents an integer of 1 to 4; $R^1$ represents a hydrogen atom, a fluorine atom, an alkyl group having 1 to 8 carbon atoms, a vinyl group, an alicyclic group, an aryl group, or a derivative of the alkyl group having 1 to 8 carbon atoms, the vinyl group, the alicyclic group, or the aryl group, when n represents 2 or less, $R^1$'s may be the same or different; and $R^2$ represents a hydrogen atom, an alkyl group having 1 to 8 carbon atoms, an allyl group, a vinyl group, or an alicyclic group, and when n represents 2 or more, $R^2$'s may be the same or different.

3. The resist composition according to claim 2, wherein the derivative contains an aryl group.

4. The resist composition according to claim 2, wherein the derivative contains an ester linkage or an ether linkage.

5. The resist composition according to claim 1, wherein the resist composition further comprises a silicone compound as an additive compound, wherein the amount of the additive compound is preferably 0.1 parts by weight to 200 parts by weight with respect to 100 parts by weight of the resin in the resist composition.

6. A method for forming a pattern, comprising:
preparing a resist composition containing
   a solvent; and
   a resin in the solvent, the resin being prepared by the hydrolysis and condensation of an alkoxy group-containing compound that contains an alkoxy group bound to a silicon atom or a germanium atom in the presence of an acid or an alkali, and a portion of the resist composition irradiated with an energy radiation being insoluble in a developing solution;
arranging the prepared resist composition on a substrate;
partially irradiating the arranged resist composition with the energy radiation; and
removing a portion of the resist composition that is not irradiated with the energy radiation from the substrate using the developing solution,
wherein the resist composition forms voids having an average size of 8 nm or less.

7. The method according to claim 6, wherein the alkoxy group-containing compound is represented by the following formula, and
the resin is prepared by the hydrolysis and condensation of at least one type of the alkoxy group-containing compound, $$R^3{}_{4-n}M^2(OR^4)_n \qquad (2)$$

where in formula (2), $M^2$ represents a silicon atom or a germanium atom; n represents an integer of 1 to 4; $R^3$ represents a hydrogen atom, a fluorine atom, an alkyl group having 1 to 8 carbon atoms, a vinyl group, an alicyclic group, an aryl group, or a derivative of the alkyl group having 1 to 8 carbon atoms, the vinyl group, the alicyclic group, or the aryl group, when n represents 2 or less, $R^3$'s may be the same or different; and $R^4$ represents a hydrogen atom, an alkyl group having 1 to 8 carbon atoms, an allyl group, a vinyl group, or an alicyclic group, and when n represents 2 or more, $R^4$'s may be the same or different.

8. The method according to claim 7, wherein the derivative contains an aryl group.

9. The method according to claim 7, wherein the derivative contains an ester linkage or an ether linkage.

10. The method according to claim 6, wherein the prepared resist composition further comprises a silicone compound as an additive compound, wherein the amount of the additive compound is preferably 0.1 parts by weight to 200 parts by weight with respect to 100 parts by weight of the resin in the resist composition.

* * * * *